(12) United States Patent
Enns et al.

(10) Patent No.: US 7,549,979 B2
(45) Date of Patent: Jun. 23, 2009

(54) SAFETY NEEDLE DEVICE

(75) Inventors: Thomas Frederick Enns, Mississauga (CA); Adnan Stetieh, Mississauga (CA)

(73) Assignee: Benlan, Inc., Oakville (CA)

( * ) Notice: Subject to any disclaimer, the term of this patent is extended or adjusted under 35 U.S.C. 154(b) by 729 days.

(21) Appl. No.: 11/197,655

(22) Filed: Aug. 4, 2005

(65) Prior Publication Data

US 2006/0030825 A1 Feb. 9, 2006

Related U.S. Application Data

(63) Continuation-in-part of application No. 10/067,511, filed on Feb. 4, 2002, now Pat. No. 6,926,693.

(51) Int. Cl.
*A61M 5/00* (2006.01)

(52) U.S. Cl. ........................ 604/263; 604/110

(58) Field of Classification Search ................ 604/111, 604/117, 192–198, 171–177, 264, 263, 110
See application file for complete search history.

(56) References Cited

U.S. PATENT DOCUMENTS

| | | | |
|---|---|---|---|
| 3,856,020 A | 12/1974 | Kovac | |
| 4,235,234 A | 11/1980 | Whitney et al. | |
| 4,380,234 A | 4/1983 | Kamen | |
| 4,631,058 A | 12/1986 | Raines | |
| 4,645,495 A | 2/1987 | Vaillancourt | |
| 4,710,176 A | 12/1987 | Quick | |
| 4,743,231 A | 5/1988 | Kay et al. | |
| 4,813,939 A | 3/1989 | Marcus | |
| 6,004,304 A | 12/1999 | Suzuki et al. | |
| 6,613,015 B2 | 9/2003 | Sandstrom et al. | |
| 7,097,637 B2 * | 8/2006 | Triplett et al. | ............... 604/192 |
| 7,351,230 B2 * | 4/2008 | Smith et al. | ................. 604/263 |
| 2004/0147881 A1 | 7/2004 | Hyun | |
| 2005/0049553 A1 | 3/2005 | Triplett | |

FOREIGN PATENT DOCUMENTS

| | | |
|---|---|---|
| CA | 2295831 | 1/1999 |
| DE | 44 26 784 A1 | 2/1995 |
| DE | 4426784 | 2/1995 |
| EP | 1116493 A1 | 7/2001 |
| GB | 2242361 | 10/1991 |
| WO | 99/03527 | 1/1999 |
| WO | 02/45574 | 6/2002 |
| WO | WO 02/45574 A2 | 6/2002 |
| WO | WO03/028784 A1 | 4/2003 |

* cited by examiner

*Primary Examiner*—Matthew F Desanto
(74) *Attorney, Agent, or Firm*—William J. Sapone; Coleman Sudol Sapone P.C.

(57) ABSTRACT

A safety needle device for percutaneous drug delivery to a patient includes a housing that is slidably mounted on a second portion of a substantially L-shaped, hollow needle for drug delivery. The housing includes a chamber provided between a sleeve portion and a passage. A forward end of the needle, which includes a tip, must deflect in order to pass through the passage into the chamber. The forward end of the needle is restricted from exiting the chamber through the sleeve portion and through the passage.

14 Claims, 6 Drawing Sheets

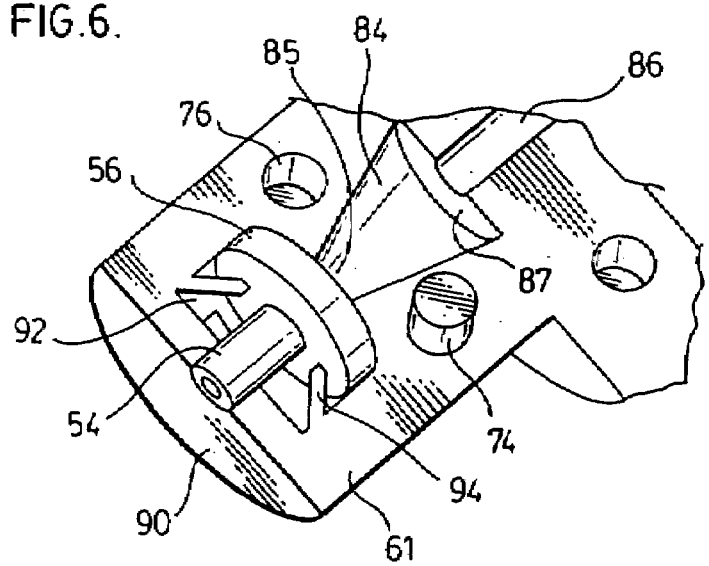
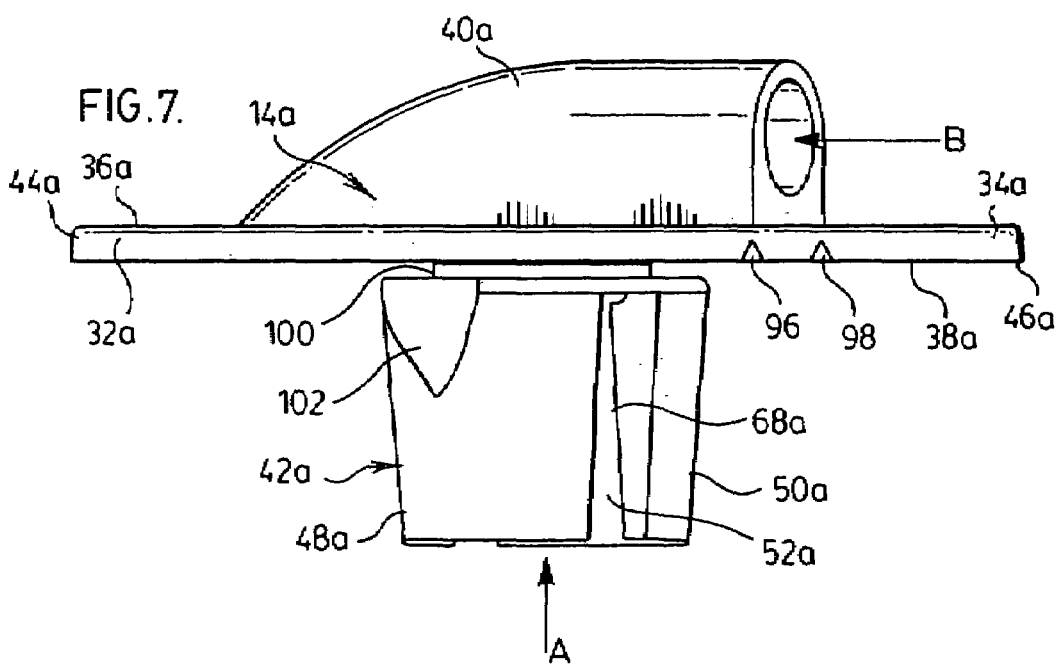

SAFETY NEEDLE DEVICE

CROSS REFERENCE TO RELATED APPLICATION

This is a continuation-in-part of U.S. patent application Ser. No. 10/067,511, filed Feb. 4, 2002.

FIELD OF THE INVENTION

The present invention relates to a safety needle device and, in particular, a safety needle device for percutaneous injection of a drug into an implanted drug delivery device having a catheter for drug delivery to a patient.

BACKGROUND OF THE INVENTION

Drug delivery devices are commonly implanted in a patient for long-term administration of drugs. These devices generally include a chamber with a self-sealing silicone septum and a catheter attached to the chamber and positioned for delivery of the drug to a suitable location, for example, into a vein. The chamber contains the drug for delivery to the patient through the catheter and is implanted such that the septum is located just under the skin of the patient. In order to access the chamber, the patient's skin and the septum of the drug delivery device are pierced using a needle and the drug is introduced into the chamber by injection using a syringe or other delivery device.

Conventional hypodermic needles are not used for the introduction of a drug to a drug delivery device for various reasons including, for example, the possibility that these needles can damage the septum. Instead, specially designed needles are used to pierce the skin and the septum. These needles include a right angle bend (approximately a ninety degree bend) for convenient access to the chamber and are designed to inhibit coring of the septum and ensure penetration of the skin and septum at approximately ninety degrees. The needles are appropriately sized to access the chamber of the device. A portion of the needle lies approximately parallel with the surface of the skin of the patient, to allow the needle to be taped down.

The needles are typically disposable and are discarded after only one use. The handling and disposal of the used needles is hazardous due to the potential risk of being injured by the sharp end of the needle. This is particularly dangerous because the needle may be contaminated and therefore capable of spreading diseases such as hepatitis and HIV, for example. A safety device for reducing injury or contamination resulting from contact with a used needle is therefore desirable.

SUMMARY OF THE INVENTION

In one aspect of the present invention there is provided a safety needle device for percutaneous drug delivery to a patient, the safety needle device including:

a substantially L-shaped, hollow needle for drug delivery therethrough, the needle having a first portion and a second portion, the second portion being aligned with a needle axis and extending substantially perpendicular to the first portion, the second portion having a forward end, the forward end including a bend and terminating at a tip, the tip being offset from the needle axis;

a handle body having a pair of opposed flexible wings for facilitating insertion of the needle into the patient and removal of the needle from the patient, a spine extends from an upper surface of the pair of opposed flexible wings and a retainer extends from a lower surface of the pair of opposed flexible wings, the first portion of the needle extending through the spine and the second portion of the needle extending downwardly from the lower surface of the pair of opposed flexible wings;

a housing slidably mounted on the second portion of the needle, the housing including a chamber provided between a sleeve portion and a passage, the forward end of the needle being slidable through the passage into the chamber, the passage being sized to force the needle into a deflected state as the tip of the needle travels toward the chamber; and wherein, the forward end is restricted from exiting the chamber through the sleeve portion and through the passage.

BRIEF DESCRIPTION OF THE DRAWINGS

The invention will be better understood with reference to the following Figures in which like numerals denote like parts and in which:

FIG. 6 is a perspective view of a portion of a housing of the safety needle device of FIG. 1;

FIG. 7 is a perspective view of a portion of a safety needle device according to another embodiment of the present invention;

DETAILED DESCRIPTION OF THE PREFERRED EMBODIMENTS

Figure 1:
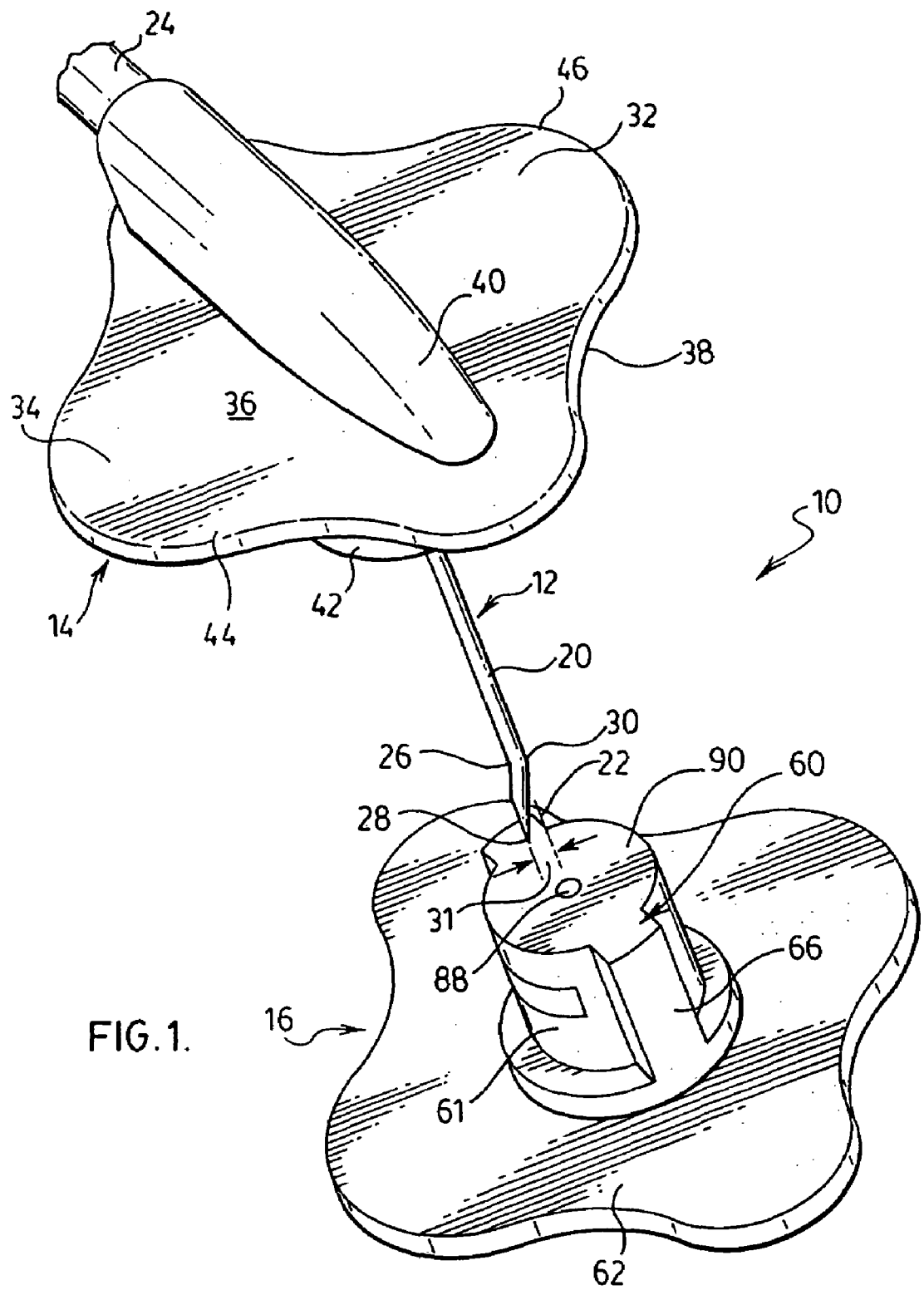
FIG. 1 is an exploded perspective view of a safety needle device according to an embodiment of the present invention.
Figure 2:
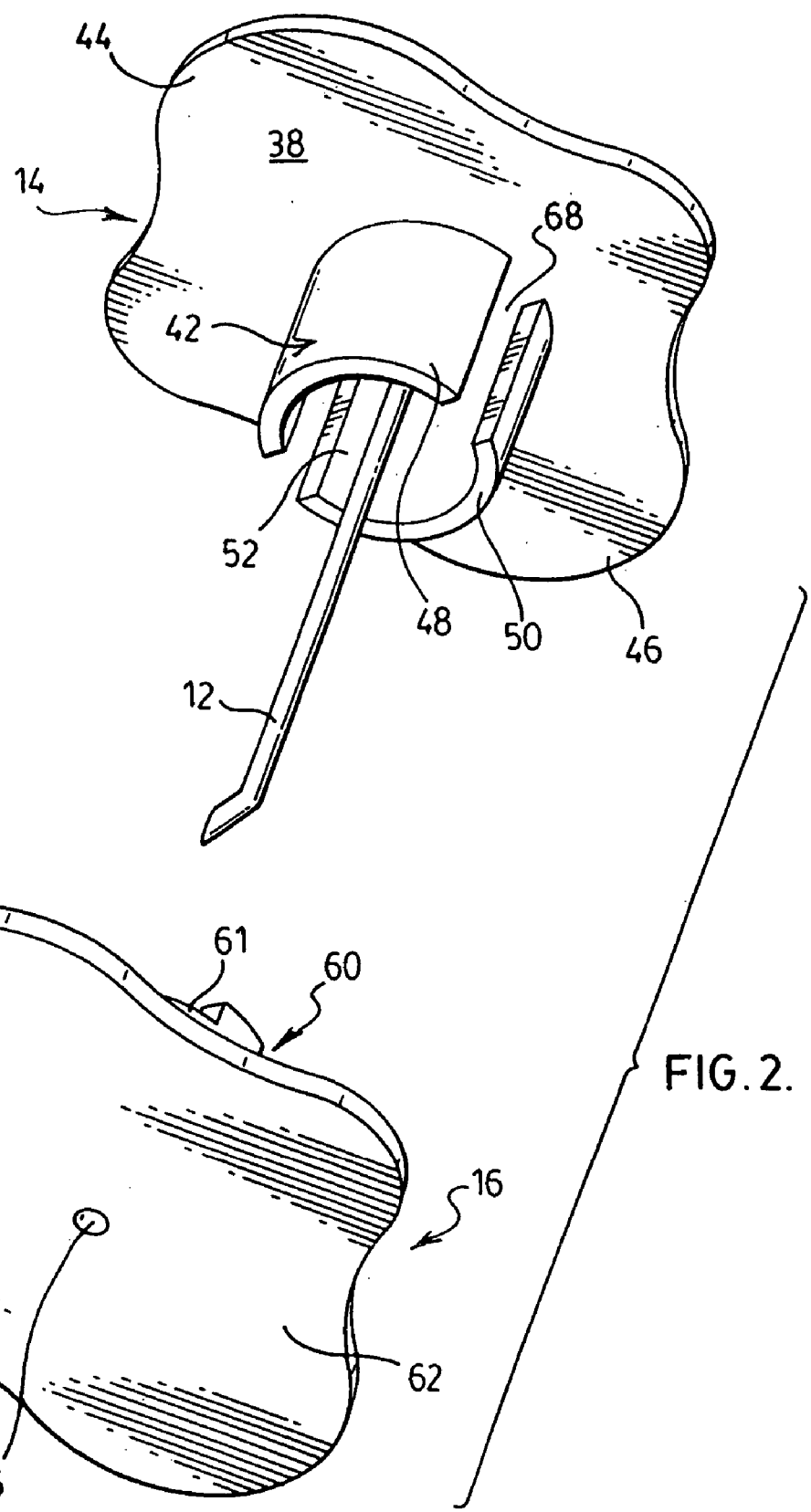
FIG. 2 is another exploded perspective view of the safety needle device of FIG. 1.
Figure 5:
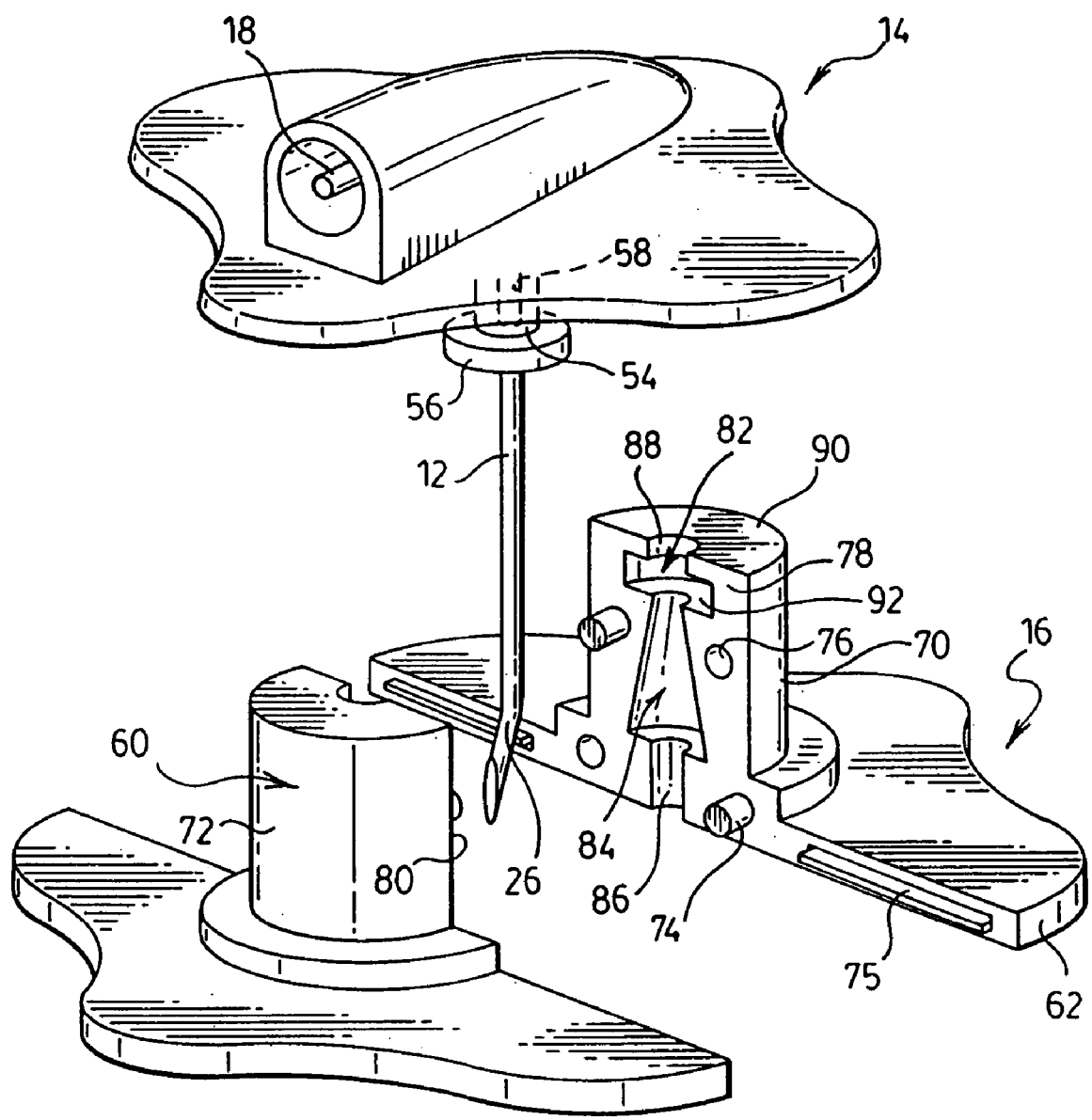
FIG. 5 is a further exploded perspective view of the safety needle device of FIG. 1.

Referring to FIGS. 1 and 2, a safety needle device 10 is generally shown. The safety needle device 10 includes a drug delivery needle 12, a handle body 14 and a housing 16. The drug delivery needle 12 is substantially L-shaped and includes a first portion 18, which is shown in FIG. 5, and a second portion 20. The second portion 20 is aligned with a needle axis 22 and extends at an angle of approximately ninety degrees with respect to the first portion 18. The needle 12 is hollow to define a continuous fluid passage through the first and second portions 18, 20, respectively.

A flexible tube 24 is coupled to the first portion 18 of the needle 12. The tube 24 extends outwardly from the handle body 14 and is coupled to a remote drug source (not shown). A drug is delivered through the flexible tube 24 into the continuous fluid passage of the needle 12. The flexible tube 24 is made of a plastic suitable for drug delivery applications.

The second portion 20 of the needle 12 includes a forward end 26, which has a tip 28. A bend 30 is provided in the forward end 26 of the needle 12 so that the tip is offset from the needle axis 22 by an offset distance 31. The forward end 26 of the needle 12 is bent to provide a non-coring needle, as will be understood by those of skill in the art. The continuous fluid passage is open at the tip 28 to allow fluid to pass therethrough and the tip 28 is sharp for piercing the skin of a patient and for piercing a septum of a chamber of a catheter, for example.

The handle body 14 is coupled to the needle 12 to allow a user to grasp the needle 12 and move it in a precise manner. The handle body 14 is a single part that is molded from a resiliently flexible plastic such as PVC (Polyvinyl Chloride), for example. The handle body 14 includes a pair of opposed wings 32, 34 having an upper surface 36 and a lower surface 38. A spine 40 projects from the upper surface 36 of the opposed wings 32, 34 and generally defines the boundary between the opposed wings 32, 34. The first portion 18 of the needle 12 extends part way through the spine 40 and the second portion 20 of the needle 12 projects downwardly from approximately the center of the handle body 14, between the pair of flexible wings 32, 34.

Figure 3:
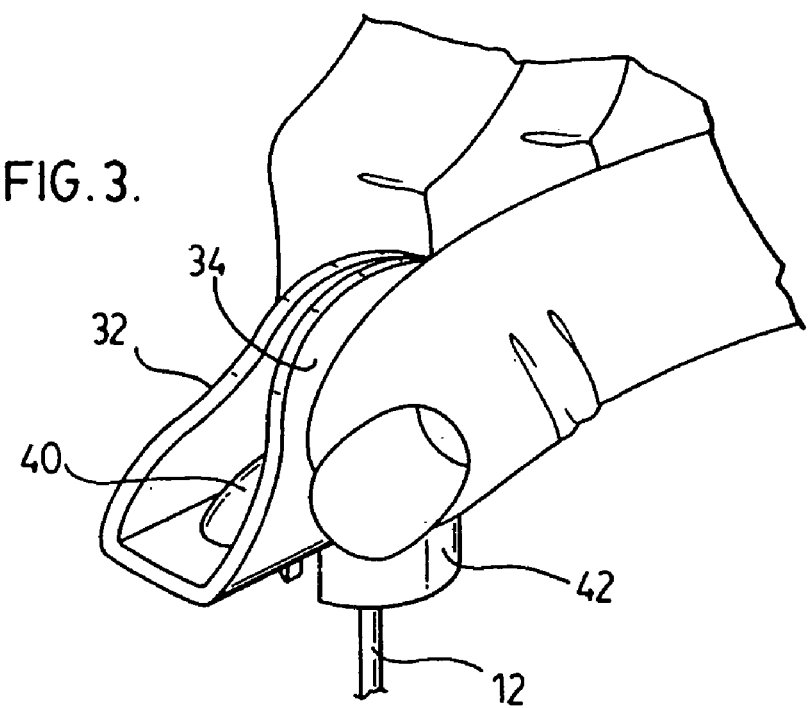
FIG. 3 is a perspective view of a portion of the safety needle device of FIG. 1.

In order to grasp the handle body 14, the wings 32, 34 are flexed upwardly so that distal ends 44, 46 of the wings 32, 34, respectively, contact one another. Thus, the wings 32, 34 are effectively pinched together when grasped, as best shown in FIG. 3. When not being used for insertion or extraction of the device 10, the wings 32, 34 return to their laterally extending state and are typically taped to the patient to steady the device 10 during the drug delivery process. It will be appreciated that the spine 40 provides rigidity to the device 10 when the needle 12 is being inserted or extracted from a patient.

The handle body 14 further includes a retainer 42 that extends from the lower surface of the wings 32, 34. The retainer 42 includes a pair of downwardly directed curved walls 48 and 50 that generally define a cylindrical recess 52. Gaps 68 are provided between the curved walls 48, 50.

Figure 4:
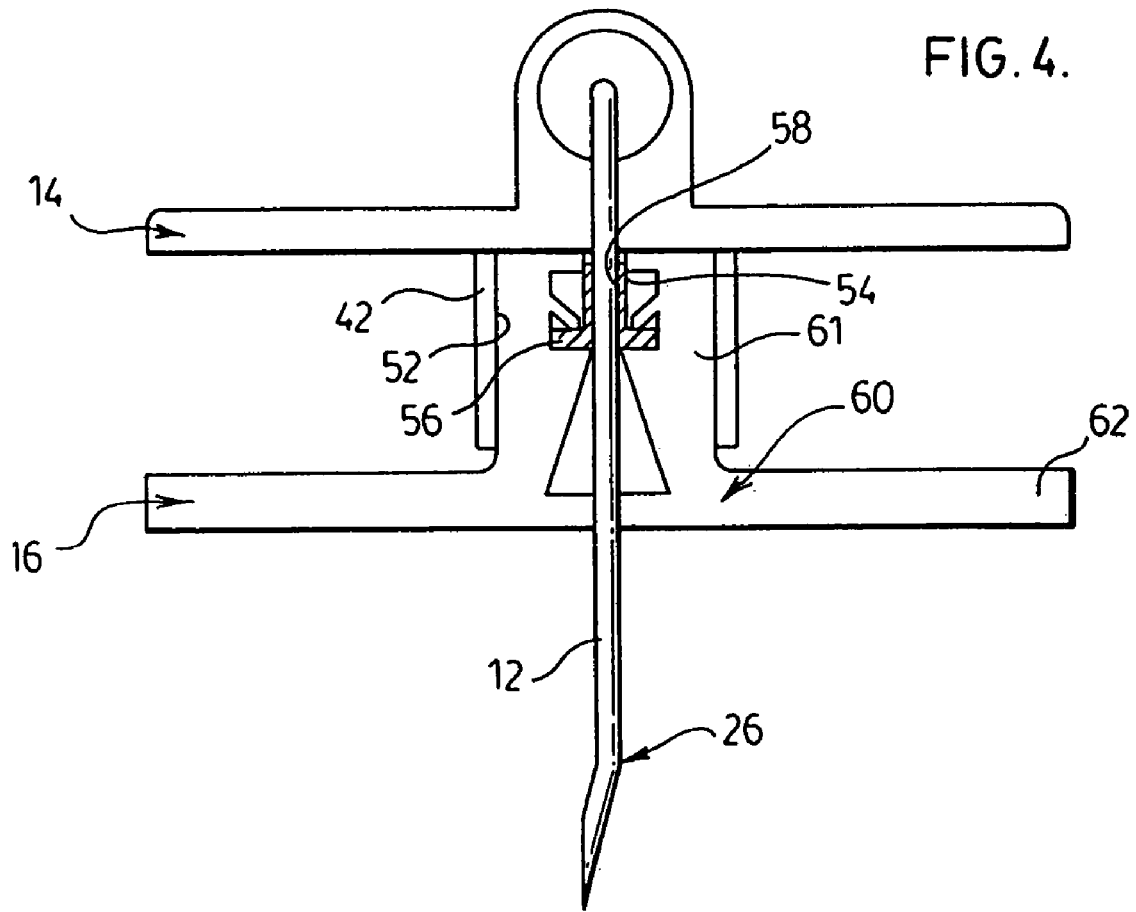
FIG. 4 is a side sectional view of the safety needle device of FIG. 1.

Prior to and during drug delivery, the housing 16 is coupled to the handle body 14, as shown in FIG. 4. The housing 16 includes a housing body 60 having a generally cylindrical post 61 that extends from a flat base 62. The post 61 is sized to be received in the cylindrical recess 52 of the handle body retainer 42. A pair of opposed projections 66, which are shown in FIG. 1, are sized to fit into the gaps 68 provided between the curved walls 48, 50 of the retainer 42. The housing body 60 is made of a generally rigid plastic, such as polycarbonate, for example.

The housing 16 further includes a sleeve 54 that is received in the housing body 60. The sleeve 54 includes a bore 58, which extends therethrough, and an outwardly extending flange 56. The diameter of the bore 58 is sized to generally prevent the forward end 26 of the needle 12 from passing through the sleeve 54 without restricting the linear portion of the needle 12 to from sliding easily therethrough. The length of the sleeve 54 is sized to provide a long support for the needle 12 so that deflection of the needle 12 occurs as described below. The sleeve 54 is made of a metal such as stainless steel, for example.

The housing body 60 consists of a first component 70 and a second component 72, as shown in FIG. 5. The first component 70 includes an inner surface 78 that abuts an inner surface 80 of the second component 72, when the housing body 60 is assembled. The components 70, 72 are coupled to one another by corresponding pins 74 and recesses 76 that are provided in the surfaces 78, 80. The pins 74 fit snugly into the recesses 76 to secure the components 70, 72 together. Male-female keys 75 are further provided in the surfaces 78, 80 to ensure that the components 70, 72 are properly aligned.

The inner surfaces 78, 80 of the respective components 70, 72 define a sleeve-receiving cavity 82, a chamber 84 and a forward passage 86. The sleeve-receiving cavity 82 includes an aperture 88, which extends through a rear end 90 of the housing body 60, and a slot 92. The slot 92 includes a pair of arms 94 that are directed toward a lower surface 93 of the slot 92. The arms 94 act as a spring to bias the outwardly extending flange 56 of the sleeve 54 toward the lower surface 93.

The chamber 84 is generally conical in shape and is sized to receive the forward end 26 of the needle 12 in an undeflected state. The chamber 84 extends between a neck 85, which is provided between the sleeve-receiving cavity 82 and the chamber 84, and a surface 87, which is generally aligned with an upper surface of the base 62. The chamber 84 is not restricted to being conical in shape. The chamber 84 may be any shape that houses an undeflected forward end 26 of the needle 12.

The forward passage 86 extends through the base 62 of the housing 16 and communicates with the chamber 84. The diameter of the forward passage 86 is sized to be less than the offset distance 31 of the needle tip 28. As such, the portion of the needle 12 that extends between the sleeve 54 and the tip 28 must deflect in order for the forward end 26 to travel through the forward passage 86. The deflection is initiated as the tip 28 travels into the forward passage 86 in the direction of the chamber 84. Upon entering the chamber 84, the forward end 28 of the needle 12 returns to its original, undeflected shape. At the same time, the arms 94 apply downward pressure to the sleeve 54, which in turn applies pressure to the bend 30 of the needle 12 to force the tip 28 of the needle 12 into abutment with the surface 87. This restricts movement of the needle 12.

The housing 16 further includes a foam pad (not shown) that is coupled to a lower surface 63 of the base 62. The foam pad is an open-celled plastic foam to allow air flow therethrough, thereby providing a layer that allows the flow of air between the molded plastic base 62 and the skin of a patient when in use.

In use, a user inserts the second portion 20 of the needle 12 into the patient using the wings 32, 34 of the handle body 14. The wings 32, 34 are then taped to the patient in order to steady the safety needle device 10 for the duration of the drug delivery process. Following injection of the drug, the user withdraws the needle 12 from the patient, again using the wings 32, 34 of the handle body 14. As the user withdraws the needle 12 with one hand, the user simultaneously presses downward on the base 62 of the housing 16 with the other hand, thereby sliding the housing 16 toward the forward end 26 of the needle 12 away from the handle body 14. The second portion 20 of the needle 12 deflects as the tip 28 enters the forward passage 86 of the housing body 60 to allow the forward end 26 of the needle 12 to slide therethrough. The forward end 26 then enters the chamber 84 and returns to its undeflected state, thereby trapping the forward end 26 of the needle 12 in the chamber 84. The safety needle device 10 is then safely disposed of.

In another embodiment of the safety needle device 10, the chamber 84 is sized to receive and maintain the forward end 26 of the needle 12 in a partially deflected state. In the partially deflected state, the needle 12 is less deflected than when it is in the deflected state passing through the forward passage 86.

It will be appreciated by a person skilled in the art that the safety needle device 10 described herein may be used with any size of non-coring needle.

Referring to FIG. 7, another embodiment of a handle body 14a for use in a safety needle device similar to safety needle device 10 of FIGS. 1-6 is shown. Similar to the handle body 14 of safety needle device 10, handle body 14a is a single part that is molded from a resiliently flexible plastic such as PVC (Polyvinyl Chloride), for example.

The handle body 14a includes a pair of opposed wings 32a, 34a having an upper surface 36a and a lower surface 38a. A spine 40a projects from the upper surface 36a of the opposed wings 32a, 34a and generally defines the boundary therebetween. Grooves 96, 98 are provided in the lower surface 38a of the opposed wings 32a, 34a and extend along the entire length thereof on opposite sides of the spine 40a. The needle (not shown) extends through the handle body 14a in a manner that has been previously described with respect to handle body 14.

Use of the handle body 14a with a safety needle device is similar to the use of handle body 14. In order to grasp the handle body 14a, the wings 32a, 34a are flexed upwardly so that distal ends 44a, 46a of the wings 32a, 34a, respectively, contact one another. Thus, the wings 32a, 34a are effectively pinched together when grasped. When not being used for insertion or extraction of the safety needle device 10, the wings 32a, 34a return to their laterally extending state and are typically taped to the patient to steady the device 10 during the drug delivery process. The grooves 96, 98 increase the range of motion and allow for less restricted movement of the wings 32a, 34a when they are flexed upwards.

A neck 100 is provided between the pair of opposed wings 32a, 34a and retainer 42a. The retainer 42 extends from the lower surface of the wings 32a, 34a. The retainer 42a includes a pair of downwardly directed curved walls 48a and 50a that generally define a cylindrical recess 52a. Gaps 68a are provided between the curved walls 48a, 50a.

Figure 8:
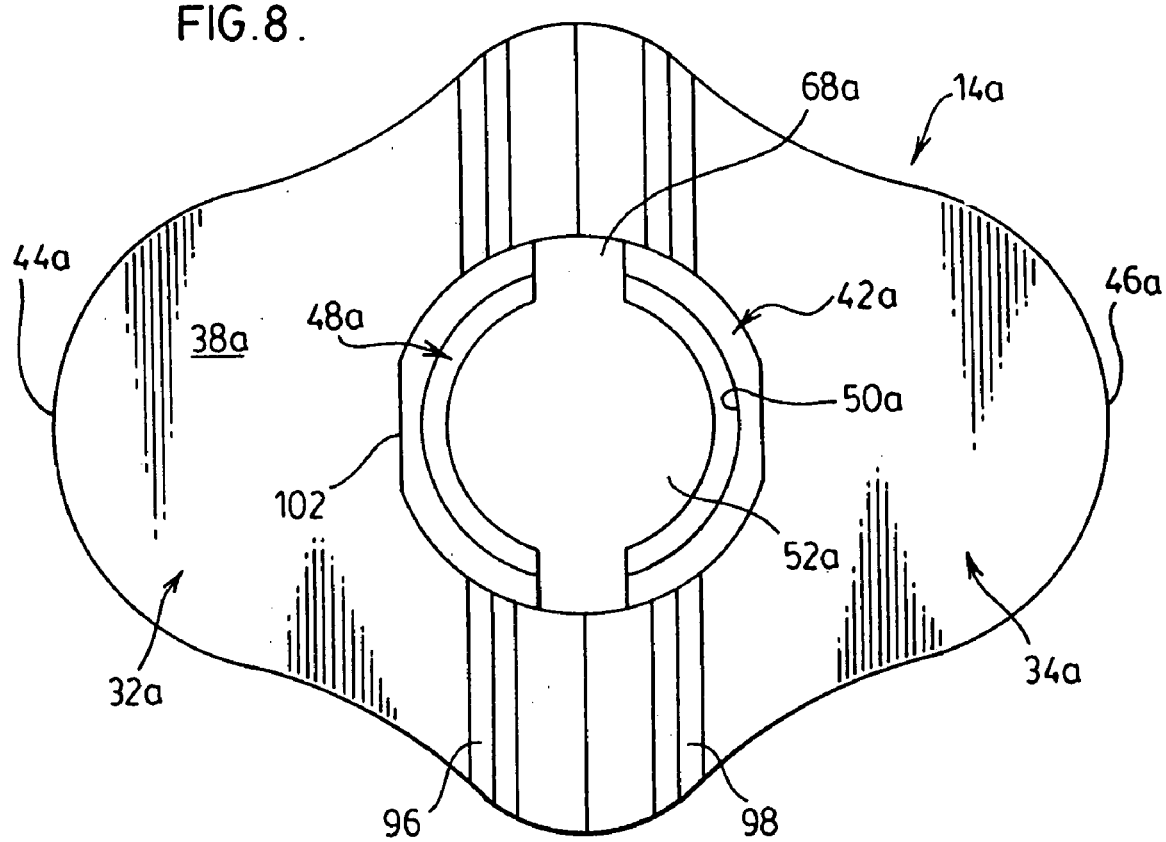
FIG. 8 is a view on A of FIG. 7.
Figure 9:
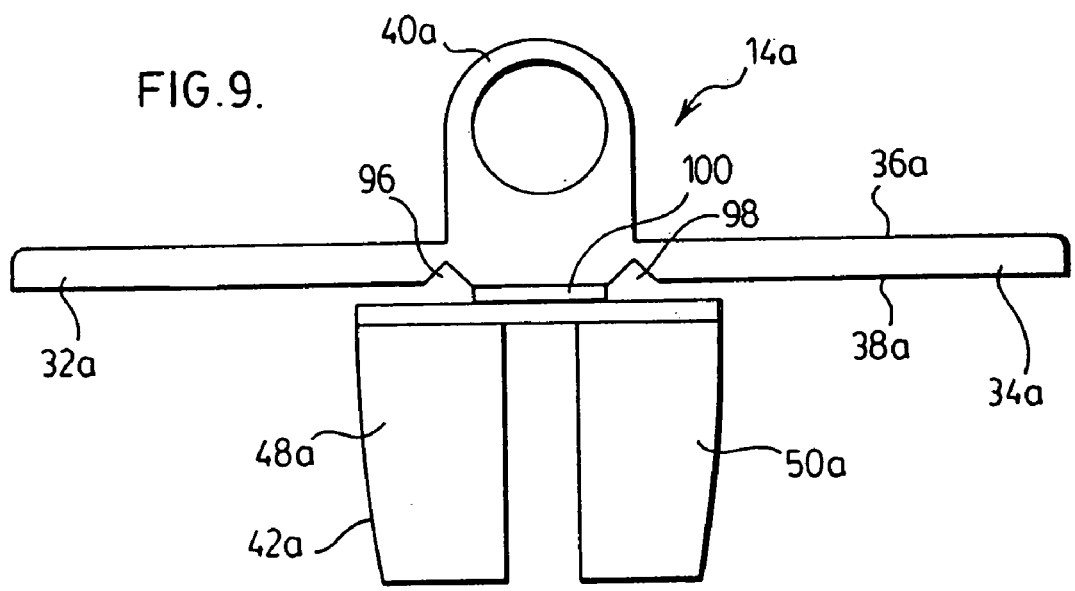
FIG. 9 is a view on B of FIG. 7.

The retainer 42a further includes flat portions 102 that are provided on each of the curved walls 48a, 50a adjacent to the neck 100. As shown in FIG. 8, the flat portions 102 are generally parallel to the grooves 96, 98. The flat portions 102 are provided to increase the range of motion of the wings 32a, 34a so that a larger portion of the wings 32a, 34a may be taped to the patient's skin during the drug delivery process. The increased contact between the patient and the handle body 14a stabilizes the safety needle device to reduce injury resulting from movement of the safety needle device while the needle is inside the patient.

Operation of the handle body 14a with a safety needle device is similar to operation of handle body 14 with safety needle device 10 and therefore will not be repeated here.

A specific embodiment of the present invention has been shown and described herein. However, modifications and variations may occur to those skilled in the art. For example, rather than housing 16 including a sleeve 54 and housing body 60, the housing 16 may be a single part having a bore that extends between upper surface 90 and chamber 84. Also, the size and shape of many of the features may vary while still providing the same function. Other modifications and variations may occur to those skilled in the art. All such modifications and variations are believed to be within the sphere and scope of the present invention.

What is claimed is:

1. A safety needle device for percutaneous drug delivery to a patient, said safety needle device comprising:
a substantially L-shaped, hollow needle for drug delivery therethrough, said needle having a first portion and a second portion, said second portion being aligned with a needle axis and extending substantially perpendicular to said first portion, said second portion having a forward end, said forward end including a bend and terminating at a tip, said tip being offset from said needle axis;
a handle body having a pair of opposed flexible wings for facilitating insertion of said needle into said patient and removal of said needle from said patient, a spine extends from an upper surface of said pair of opposed flexible wings and a retainer extends from a lower surface of said pair of opposed flexible wings, said first portion of said needle extending through said spine and said second portion of said needle extending downwardly from said lower surface of said pair of opposed flexible wings;
a housing slidably mounted on said second portion of said needle, said housing including a chamber provided between a sleeve which resides in the housing above the chamber and a passage disposed below the chamber, said chamber sized for receiving said forward end of said needle in at least a partially undeflected state such that said needle tip when in said chamber is out of alignment with said passage, said forward end of said needle being slidable through said passage into said chamber, said passage being sized to force said needle into a deflected state as said tip of said needle travels toward said chamber;
wherein, said forward end is restricted from exiting said chamber in an upward direction by said sleeve and in a downward direction by the needle tip being out of alignment with said passage, said sleeve portion having a bore sized to restrict passage of said bend of said forward end therethrough, the sleeve having a length cooperating with the housing to hold the needle substantially in alignment with the needle axis to maintain said bent forward end within said chamber when said tip of said needle is received in the chamber.

2. A safety needle device as claimed in claim 1, wherein said chamber is sized to receive said forward end of said needle in an undeflected state.

3. A safety needle device as claimed in claim 2, wherein said sleeve has an outwardly extending flange that is received in a housing body of said housing.

4. A safety needle device as claimed in claim 3, wherein said housing body includes a post that extends from a base, said post being received in said retainer of said handle body to couple said housing to said handle body.

5. A safety needle device as claimed in claim 4, wherein said housing is movable away from said handle body by applying a force to said base in the direction of said needle tip.

6. A safety needle device as claimed in claim 5, wherein said housing body includes two components that are coupled to one another.

7. A safety needle device as claimed in claim 3 wherein said housing further includes a pair of arms in contact with said outwardly extending flange of said sleeve to apply downward pressure to the sleeve, thereby applying pressure to the bend of the forward end so as to bias said tip of said needle toward a lower surface of said chamber to restrict movement of said forward end of said needle in said chamber.

8. A safety needle device as claimed in claim 2, wherein said chamber is generally conical in shape.

9. A safety needle device as claimed in claim 1, wherein said retainer is a pair of curved walls.

10. A safety needle device as claimed in claim 9, wherein each of said pair of curved walls includes a flat portion, said flat portion being provided to increase the range of motion of the opposed flexible wings in the downward direction.

11. A safety needle device as claimed in claim 1, further comprising a pair of grooves provided in said lower surface of said opposed flexible wings.

12. A safety needle device as claimed in claim 11, wherein said grooves increase the flexibility of said opposed flexible wings.

13. A safety needle device as claimed in claim 1, wherein said chamber is sized to maintain said forward end of said needle in a partially deflected state.

14. A safety needle device as claimed in claim 1 further comprising biasing means for applying downward pressure to the sleeve, thereby applying pressure to the bend of the forward end so as to bias said tip of said needle toward a lower surface of said chamber to restrict movement of said forward end of said needle in said chamber.

* * * * *